United States Patent
Schwertfeger et al.

(10) Patent No.: US 8,394,989 B2
(45) Date of Patent: *Mar. 12, 2013

(54) FLUORINATED OXY-CARBOXYLIC ACIDS, DERIVATIVES, AND METHODS OF PREPARATION

(75) Inventors: Werner Schwertfeger, Langgons (DE); Klaus Hintzer, Kastl (DE); Egon Obermaier, Taubenbach (DE)

(73) Assignee: 3M Innovative Properties Company, Saint Paul, MN (US)

( * ) Notice: Subject to any disclaimer, the term of this patent is extended or adjusted under 35 U.S.C. 154(b) by 390 days.

This patent is subject to a terminal disclaimer.

(21) Appl. No.: 12/677,339

(22) PCT Filed: Sep. 26, 2008

(86) PCT No.: PCT/US2008/077834
§ 371 (c)(1),
(2), (4) Date: Mar. 10, 2010

(87) PCT Pub. No.: WO2009/042853
PCT Pub. Date: Apr. 2, 2009

(65) Prior Publication Data
US 2010/0197963 A1    Aug. 5, 2010

Related U.S. Application Data

(60) Provisional application No. 60/975,696, filed on Sep. 27, 2007.

(51) Int. Cl.
*C07C 51/58* (2006.01)
*C07C 53/38* (2006.01)

(52) U.S. Cl. .................................. 562/851; 562/849

(58) Field of Classification Search .................... None
See application file for complete search history.

(56) References Cited

U.S. PATENT DOCUMENTS

| | | | |
|---|---|---|---|
| 3,525,724 A | 8/1970 | Squire | |
| 3,950,262 A * | 4/1976 | Lalancette | 252/186.24 |
| 4,035,434 A * | 7/1977 | Rodewald | 528/408 |
| 4,987,254 A * | 1/1991 | Schwertfeger et al. | 562/851 |
| 5,144,092 A | 9/1992 | Marraccini | |
| 5,220,076 A | 6/1993 | Marraccini | |
| 5,488,181 A | 1/1996 | Marchionni | |
| 5,777,174 A | 7/1998 | Marchionni | |
| 5,798,417 A | 8/1998 | Howard, Jr. | |
| 5,942,572 A | 8/1999 | Chittofrati | |
| 6,013,747 A | 1/2000 | Abusleme | |
| 6,046,368 A | 4/2000 | Lamanna | |
| 6,080,795 A | 6/2000 | Pantini | |
| 6,083,424 A | 7/2000 | Fontana | |
| 6,174,979 B1 | 1/2001 | Biancardi | |
| 6,262,006 B1 | 7/2001 | Silvani | |
| 6,265,494 B1 | 7/2001 | Wlassics | |
| 6,277,906 B1 | 8/2001 | Biancardi | |
| 6,359,044 B1 | 3/2002 | Biancardi | |
| 6,417,390 B1 | 7/2002 | Abusleme | |
| 6,509,509 B2 | 1/2003 | Tonelli | |
| 6,573,411 B2 | 6/2003 | Russo | |
| 6,660,798 B1 | 12/2003 | Marchese | |
| 6,821,454 B2 | 11/2004 | Visca | |
| 6,869,920 B2 | 3/2005 | Marchionni | |
| 6,963,013 B2 | 11/2005 | Navarrini | |
| 7,132,051 B2 | 11/2006 | Marchionni | |
| 7,160,967 B2 | 1/2007 | Navarrini | |
| 2006/0122301 A1 | 6/2006 | Nair | |

FOREIGN PATENT DOCUMENTS

| | | |
|---|---|---|
| EP | 0354419 | 2/1990 |
| GB | 1294657 | 11/1972 |
| JP | 6293704 | 10/1994 |
| SU | 1100277 | 6/1984 |
| WO | WO 2009/042331 | 4/2009 |

OTHER PUBLICATIONS

Marchionni, "Synthesis and Characterization of Perfuoropolyethers from Perfluoromethylvinylether", Journal of Fluorine Chemistry, 1999, vol. 95, p. 85-95.
Written Opinion of the ISA for International Application No. PCT/US2008/077834, 5 pgs.
International Search Report for PCT/US2008/077834; 3 pgs.
Lewis, Richard J. Sr., Hawley's Condensed Chemical Dictionary, Twelfth Edition, pp. 696-697, 1993.

* cited by examiner

*Primary Examiner* — Karl J Puttlitz
(74) *Attorney, Agent, or Firm* — C. Michael Geise

(57) ABSTRACT

Provided are fluorinated oxy-carboxylic acids, derivatives of oxy-carboxylic acids, and methods of preparing oxy-carboxylic acids and derivatives thereof.

11 Claims, No Drawings

FLUORINATED OXY-CARBOXYLIC ACIDS, DERIVATIVES, AND METHODS OF PREPARATION

CROSS-REFERENCE TO RELATED APPLICATION

This application is a national stage filing under ±U.S.C. §371 of PCT/US2008/077834, filed Sep. 26, 2008, which claims priority to U.S. Provisional Patent Application No. 60/975,696, filed Sep. 27, 2007, the disclosure of which is incorporated by reference in its/their entirety herein.

SUMMARY

The present description relates to fluorinated oxy-carboxylic acids and derivatives thereof, and to the preparation of fluorinated oxy-carboxylic acids from fluorinated ethers.

Fluorinated carboxylic acids and derivatives thereof have a number of industrial uses, including, for instance, as emulsifiers in the preparation of fluoropolymers. Further, fluorinated carboxylic acids in the form of their acid fluorides may be useful in the synthesis of fluorinated ethers.

The present description provides, in one aspect, a process comprising reacting, at a reaction temperature, a fluorinated ether of the formula (I)

$$R_f\text{—O—}(CF_2)_a\text{—CF}=CF_2 \qquad (I)$$

wherein $R_f$ is a fluorinated linear or branched aliphatic group and a is either 1 or 0, with an oxygen-containing gas in the presence of a graphite intercalated by a Lewis acid catalyst such as, for example, $SbF_5$ to yield a fluorinated oxy-carboxylic acid fluoride.

In another aspect, the present description provides a process comprising reacting a fluorinated ether of formula (I)

$$R_f\text{—O—}(CF_2)_a\text{—CF}=CF_2 \qquad (I)$$

wherein $R_f$ is a fluorinated linear or branched aliphatic group and a is either 1 or 0, with an oxygen-containing gas in the presence of a Lewis acid catalyst at a temperature of at least 70° C. to yield a fluorinated oxy-carboxylic acid fluoride.

DETAILED DESCRIPTION

It has been found that fluorinated ethers may react to yield fluorinated oxy-carboxylic acid fluorides. The reactions described herein are carried out in the presence of an oxygen-containing gas and a Lewis acid catalyst.

Oxygen-containing gas includes, for instance, pure oxygen, oxygen diluted in a non-reactive carrier gas such as nitrogen, and air. Other oxygen delivering materials such as, for example, inorganic peroxo compounds may be used as well.

In some embodiments, fluorinated ethers described herein are those having the formula (I)

$$R_f\text{—O—}(CF_2)_a\text{—CF}=CF_2 \qquad (I)$$

wherein $R_f$ is a fluorinated linear or branched aliphatic group and a is either 1 or 0. By aliphatic group, it is meant an alkyl group, an aryl group, a cycloalkyl group, an aralkyl group, a cyclic aralkyl group, and the like. Any of these groups may optionally be interrupted by one or more oxygen atoms. By "interrupted by one or more oxygen atoms", is meant that the aliphatic groups may contain ether linkages.

In particular embodiments, fluorinated ethers described herein are those having an $R_f$ according to the formula (III)

$$A\text{—}(OCF(R^2_f)CF_2)_n\text{—}(O(CF_2)_m)_p\text{—} \qquad (III)$$

where each n is from 0 to 10; each m is from 1 to 10, each p is from 0 to 10; A is selected from X and $XC_aF_{2a}$, where X is a halogen, hydrogen, or a functional group such as $SO_2Y$ (with Y being F or CO or COOR' with R' being lower alkyl like methyl or ethyl, and a is from 1 to 10; and $R^2_f$ is a fluorinated aliphatic group of from 1 to 10 carbon atoms. It should be understood that, as used in formula (III) where the phrase "each m is from 0 to 10" is used, it is meant that if p is greater than 1, then each value of m included in a repeated unit p is independently chosen from 1 to 10. Not all values of m in a given molecule need be the same. For instance, for a particular embodiment of formula (III):

$$CF_3\text{—}(OCF(CF_3)CF_2)_n\text{—}(OCF_2)\text{—}(OCF_2CF_2CF_2)\text{—}$$

p is equal to two, $R^2_f$ is $CF_3$, and therefore there are two values for m, in this instance, one is 1 and the other is 3. Accordingly, each is selected from 1 to 10, but not every value of m is the same.

In particular embodiments of formula (III), X may be F and a may be from 1 to 4. In such embodiments, the terminal chain length of the $R_f$ group is not more than four carbons long. Examples of such embodiments include, for instance, $CF_3$—O—$(CF_2)_3$—O—, corresponding to the fluorinated ether $CF_3$—O—$(CF_2)_3$—O—$(CF_2)_a$—CF=$CF_2$ with a being defined as above.

In yet further embodiments, X is F, a is from 1 to 4, and m is from 1 to 4. Other embodiments include those in which n is 0. In such cases, the corresponding fluorinated ether is a linear fluorinated ether that contains no $R^2_f$ groups.

Additional embodiments of formula (III), and thus the ethers of formula (I), include those wherein X is Br. When X is Br, for instance, the ether described can be further functionalized. Such further functionalization may take place either before or after the reaction of the ether of formula (I) to yield a fluorinated oxy-carboxylic acid.

Such further functionalization may include grafting onto a polymer the ether of formula (I) or the resulting reacted fluorinated oxy-carboxylic acid fluoride described below in formula (II) (or derivative thereof). Such grafting reactions may self-stabilize the oxy-carboxylic acid or derivative thereof. Accordingly, the result may be a functionalized polymer containing grafted acid fluoride units. Such functionalized polymers may themselves be useful as surfactants in emulsion polymerization reactions of fluorinated monomers (optionally copolymerized with non-fluorinated monomers). One potential advantage to such functionalized polymers may be that the resultant fluorinated polymers from the emulsion polymerization reactions may have low levels of extractable materials.

When X is Br, the resultant oxy-carboxylic acid fluorides or derivatives thereof may further present an ability for the resultant oxy-carboxylic acid fluorides or derivatives thereof to act as a surfactant in the polymerization of fluorinated monomers (optionally copolymerized with non-fluorinated monomers). Such brominated oxy-carboxylic acid fluorides or derivatives thereof may act as a chain transfer agent in the polymerization reactions described. As a result, such polymerization reactions may lead to fluoropolymers of lower molecular weight than fluoropolymers prepared in the presence of non bromine-containing oxy-carboxylic acid fluorides or derivatives thereof.

In further particular embodiments, X is F. When X is F, the oxy-carboxylic acid fluorides or derivatives thereof is relatively stable to reactions other than the formation of carboxylic acid fluoride derivatives, or further reaction of the acid fluoride or acid fluoride derivatives.

The fluorinated ethers described by formula (I) and further described in formula (III) may be converted to a oxy-carboxylic acid fluoride by reaction with an oxygen-containing gas in the presence of a catalytic amount of graphite intercalated by $SbF_5$. In some embodiments, the fluorinated ethers described by formula (I) may be converted to oxy-carboxylic acid fluorides given by the formula (II)

$$R'_f-O-(CF_2)_a-CF_2COF \quad (II)$$

wherein $R'_f$ is a fluorinated linear or branched aliphatic group and a is either 1 or 0. Preferably, $R'_f$ is the same as $R_f$ from formula (I).

In some embodiments, $R'_f$ may be given by the formula (IV):

$$A'O-(OCF(R'^2_f)CF_2)_{n'}-(O(CF_2)_{m'})_{p'}- \quad (IV)$$

where each n' is from 0 to 10; each m' is from 1 to 10, each p' is from 0 to 10; A' is selected from X' and $X'C_{a'}F_{2a'}$, where X' is a halogen, hydrogen or a functional group like $SO_2Y$ (with Y being F or Cl) or COOR' with R' being lower alkyl like methyl or ethyl, and a' is from 1 to 10; and $R'^2_f$ is a fluorinated aliphatic group of from 1 to 10 carbon atoms. It should be understood that, as used in formula (III) where the phrase "each m' is from 0 to 10" is used, it is meant that if p' is greater than 1, then each value of m' included in a repeated unit p' is independently chosen from 1 to 10. Not all values of m' in a given molecule need be the same. For instance, for a particular embodiment of formula (IV):

$$CF_3-(OCF(CF_3)CF_2)_{n'}-(OCF_2)-(OCF_2CF_2CF_2)-$$

p' is equal to two, $R'^2_f$ is $CF_3$, and therefore there are two values for m', in this instance, one is 1 and the other is 3. Accordingly, each is selected from 1 to 10, but not every value of m is the same.

In particular embodiments of formula (IV), X' may be F and a' may be from 1 to 4. In such embodiments, the terminal chain length of the $R'^2_f$ group is not more than four carbons long. Examples of such embodiments include, for instance, $CF_3-O-(CF_2)_3-O-$, corresponding to the oxy-carboxylic acid fluoride $CF_3-O-(CF_2)_3-O-(CF_2)_nCOF$, with n being either 1 or 2.

In yet further embodiments of Formula (IV), X' is F, a' is from 1 to 4, and m' is from 1 to 4. Other embodiments include those in which n' is 0. In such cases, the corresponding oxy-carboxylic acid fluoride is linear and contains no $R'^2_f$ groups.

In a further aspect, the present invention comprises converting the fluorinated oxy-carboxylic acid fluoride to a derivative selected from a carboxylic acid, an ester, an amide, and a carboxylate salt. In particular, at the end of reacting at a reaction temperature, a fluorinated ether with an oxygen-containing gas, as described herein, the reactor may be cooled to room temperature. The end of the reaction may be indicated by a negligible exotherm and an unusual pressure increase indicating the cessation of consumption of the oxygen-containing gas by the reaction system. Another test for whether the end of the reaction has been reached may be a pressure drop after the oxygen line has been closed; so long as a pressure drop is observed, the reaction is not complete and the oxygen-containing gas may be further fed into the reaction system. Due to the toxicity and high reactivity of acid fluorides, however, it may be preferable to carry out purification of the reaction product not on the acid fluoride itself, but on an acid fluoride derivative. Suitable derivatives are known to those of skill in the art and include carboxylic acids, esters, amides, and carboxylate salts.

The purification of the acid fluoride reaction product (sometimes referred to in the art as the "work up"), may include, for instance, first adding a nucleophilic compound capable of forming an acid fluoride derivative. For instance, to form an ester, an aliphatic alcohol may be added. To form a carboxylic acid or carboxylate salt, water may be added and the pH may be adjusted accordingly. To form an amide, ammonia or a primary or secondary amine may be added.

In a particular embodiment, excess alcohol (for instance, methanol) may be pumped into the reactor. The reactor may be cooled to room temperature first. The conversion of the acid fluoride to the acid fluoride derivative is exothermic, causing a temperature rise, which may be controlled by suitable cooling mechanisms. Further addition of water results in a separation of the reaction product into two phases. The lower phase contains the desired acid fluoride derivative (in this instance, the ester and/or the corresponding carboxylic acid or carboxylate salt). Further reaction of the separated lower phase with methanol, water, and acid, followed by flash distillation, may result in a further two phase distillate. The upper phase of the distillate may be returned to the distillation flask, while the lower phase may be separated to yield the ester, for instance, by subsequent fractionation.

In another embodiment, excess alcohol may be added to the reactor as described above. Further, an amine (such as trialkylamine e.g. triethylamine) may be pumped into the reactor in a molar amount that is close to one third of the generated HF (to neutralize pH of the system). Water may optionally be added to this mixture. Upon this separation, the lower phase, containing the desired acid fluoride derivative, is further treated as described above. Further reaction of the separated lower phase with methanol, water, and acid, followed by flash distillation, may result in a further two phase distillate. The upper phase of the distillate may be returned to the distillation flask, while the lower phase may be separated to yield the ester, for instance, by subsequent fractionation.

In yet another embodiment, aqueous metal hydroxide (for instance, potassium or sodium hydroxide) solution may be pumped into the reactor in an amount to ensure that the resultant pH value of the reactor is greater than 7 after the feed. In this embodiment, the reactor content separates into three phases. The lower most aqueous phase contains the carboxylate salt derivative of the acid fluoride. This later may be separated from the other two layers. Further reaction of the separated lower phase with methanol, water, and acid, followed by flash distillation, may result in a further two phase distillate. The upper phase of the distillate may be returned to the distillation flask, while the lower phase may be separated to yield the ester, for instance, by subsequent fractionation. In general, the work-up further yields a heavy phase with high viscosity.

Lewis acid catalysts described herein may be any type of Lewis acid catalyst known in the art. Such catalysts include, for instance, boron-containing Lewis acids. Boron-containing Lewis acids include those of the general formula $BZ_3$, where Z is selected from F and an alkoxide (e.g., $BF_3$, $B(OCH_3)_3$, etc). From a practical standpoint, one of ordinary skill in the art will recognize the preference to use Boron-containing Lewis acids with oxygen-containing solvents such as alcohols and ethers. The Boron-containing Lewis acids themselves may be a gas under normal handling conditions, such gas may give off toxic or otherwise undesirable fumes. Furthermore, the Lewis acid-solvent liquid complexes may be easier to handle.

In some embodiments, the Lewis acids may be intercalated into a non-reactive material. Such non-reactive materials include graphite. For instance, when the Lewis acid $SbF_5$ is used, it may be intercalated into graphite. Neat $SbF_5$ produces fumes and may not be easy to handle. Accordingly, by intercalating $SbF_5$ into graphite, the present invention provides a catalyst system that is easier and safer to handle than neat $SbF_5$. In some further embodiments, using a Lewis acid intercalated into a non-reactive material may allow for better temperature control during the reaction of the fluorinated ether with the oxygen-containing gas, thereby avoiding or at least minimizing the resultant exotherm, putting less stress on the reactor system and allowing a more uniform reaction condition (e.g., avoiding localized heating and temperature spikes during reaction).

Surprisingly, the present description shows that such intercalated Lewis acid catalysts display suitable reactivity despite their intercalation into non-reactive media.

A catalytic amount of Lewis acid catalyst may be used in the processes described herein. A catalytic amount may be, for instance, from 0.01 to 20 mol %, based upon the amount of fluorinated ether used in the reaction.

In one embodiment, the process relates to reacting a fluorinated ether of formula (I) with an oxygen-containing gas or oxygen delivering substance like inorganic peroxides (also referred to herein as inorganic peroxo compounds) in the presence of a Lewis acid catalyst at a temperature of at least 70° C. to yield a fluorinated oxy-carboxylic acid fluoride. In yet further embodiments, the reaction may be carried out at from 70 to 200° C., from 70 to 150° C., or even from 70 to 100° C. In some embodiments, the temperature is kept as low as possible to yield reaction of the fluorinated ether with the oxygen containing gas. Maintenance of a low temperature may help to inhibit explosion of the oxygen-containing reaction system (due to rapid exothermic heat generation, combustion of reactor constituents, or a combination thereof). Thus, in some embodiments, it may be preferred that the temperature of the reactor is controlled during the reaction. In particular, it may be preferred to keep the temperature of the reactor within 50° C. of the starting temperature, within 30° C. of the starting temperature, within 10° C. of the starting temperature, even within 2° C. of the starting temperature.

In other embodiments, for instance, when a catalytic amount of graphite intercalated by $SbF_5$ is used as the Lewis acid catalyst, control of the reaction temperature may not be as critical. However, it may be observed in some embodiments that the use of graphite intercalated by $SbF_5$ allows for a high degree of control over the reaction temperature, for instance, keeping the reaction temperature within 5° C. of the starting temperature.

The oxygen pressure in the reactor is, in principle, not critical for the reaction and may vary from negligible amounts to several bar. But, according to the potential risk of explosion caused by the uncontrolled reaction of the fluorinated ether with oxygen, it is preferred to keep the oxygen pressure as low as possible without limiting the rate of reaction.

In some embodiments, the processes described herein may yield improvements in the production of oxy-carboxylic acid fluorides. For instance, the processes described herein may allow for improved conversion of fluorinated ether to the corresponding oxy-carboxylic acid fluoride. Furthermore, by allowing for better control of reaction temperature, some embodiments of the processes described herein lower the risk of explosion.

EXAMPLES

General Description of the Procedure

The reactions were, unless otherwise noted, carried out in a stainless steel pressure vessel. The reactor was equipped with a stirrer, heating/cooling jacket, and temperature and pressure probes.

The dry reactor was flushed with nitrogen to remove oxygen. The fluorinated ether was a pumped into the reactor. The addition of the catalyst depended on the physical state of the compound. Solids were placed in the reactor before flushing with nitrogen, liquids were pumped in, and gases were added via a line directly from the cylinder.

Where noted, the reactor was pressurized with nitrogen to dilute the oxygen fed later.

The stirrer was started and adjusted to the desired speed rate.

After heating the reactor to the predetermined reaction temperature, oxygen was fed to the reactor. Usually less than 1 bar pressure increase was allowed on the initial oxygen feed.

Start of the reaction was indicated by an exotherm and pressure drop. The reaction generally did not start immediately. There was a delay observed which varied from several minutes to several hours.

As soon as the reaction had started, the oxygen feed was resumed. During the oxygen feed a pressure increase was observed which was not caused by the oxygen feed but mainly by the formation of fluorophosgene as side product.

The feed rate of oxygen was controlled to ensure a low oxygen content in the reactor. The end of the reaction was indicated by a negligible exotherm and an unusual pressure increase.

Another indicator for the end of reaction was a pressure drop upon closing the oxygen feed. As long as the pressure drop was observed, the reaction was continuing and thus the oxygen feed was resumed.

After the end of the oxygen feed, the reactor was cooled to room temperature followed by a work-up procedure. Due to the toxicity and the high reactivity of acid fluorides, a direct purification of the acid fluorides was not desirable.

One of the following work up procedures was used:
a) Excess of alcohol (e.g. methanol) was pumped into the reactor at room temperature. The conversion caused an exotherm which was controlled by cooling. Addition of water resulted in two phases which were separated. The lower phase contained the desired ester and/or the corresponding acid. Reaction of the lower phase with methanol, water, and sulphuric acid, followed by a flash distillation, resulted in a two phase distillate. The upper phase was returned to the distillation flask, while the lower phase was separated. Purification of the crude ester was achieved by fractionation.
b) Alcohol was added to the reactor according to a). Trialkylamine (e.g. trimethylamine) was pumped into the reactor in a molar amount that was close to one third of the generated HF. Where indicated, water was further added to the mixture. The reaction mixture consisted of two phases. The lower phase contained the desired ester and/or the corresponding acid. Reaction of the lower phase with methanol, water, and sulphuric acid, followed by a flash distillation, resulted in a two phase distillate. The upper phase was returned to the distillation flask, while the lower phase was separated. Purification of the crude ester was achieved by fractionation.
c) Aqueous potassium hydroxide solution was pumped into the reactor in an amount to ensure a pH value of greater than 7 after the feed. The reactor contents formed three phases. The lower aqueous phase contained the fluorinated acid salt formed in the oxidation reaction. The lower phase contained the desired acid in form of its potassium salt. Reaction of the lower phase with methanol, water, and sulphuric acid, followed by a flash distillation, resulted in a two phase distillate. The upper phase was returned to the distillation flask, while the lower phase was separated. Separation of the crude ester was achieved by fractionation. In addition there is a heavy phase with high viscosity.

Example 1

4491 g $CF_3O(CF_2)_3OCF=CF_2$ (MV31) was reacted with 270 g of oxygen in the presence of 10 g $SbF_5$/graphite (50% $SbF_5$) at 80° C. Work up according to procedure a) including fractionation resulted in 2229 g of $CF_3O(CF_2)_3OCF_2COOCH_3$. In addition 30 g of high boiling oil was received. Conversion of MV31 was about 90%.

Example 2

Example 1 was repeated using 4854 g MV31, 304 g oxygen, and 10.5 g $SbF_5$/graphite at 85° C. Work up according to procedure a) including fractionation resulted in 2487 g $CF_3O(CF_2)_3OCF_2COOCH_3$ and 264 g high boiling oil. Conversion of MV31 was about 95%.

Example 3

Example 1 was repeated using 3977 g MV31, 244 g oxygen, and 10.9 g $SbF_5$/graphite at 75° C. Work up including fractionation resulted in 1815 g $CF_3O(CF_2)_3OCF_2COOCH_3$ and 253 g high boiling oil. Conversion of MV31 was about 90%.

Example 4

3264 g MV31 was reacted with 200 g of oxygen. 18 g of BF3 was used as catalyst. Reaction temperature was 80° C. Work up according to method a) including fractionation resulted in 1471 g $CF_3O(CF_2)_2OCF_2COOCH_3$ and 360 g high boiling oil. Conversion of MV31 was about 95%.

Example 5

Example 4 was repeated using 3734 g MV31, 220 g of oxygen and 14 g $BF_3$ at 75° C. Work up according to method a), omitting the fractionation, resulted in 3651 g of crude ester which contained 5% MV31, 13% methanol, 20% $CF_3OCF_2CF_2COOCH_3$, and 56% $CF_3O(CF_2)_3OCF_2COOCH_3$ according to GC analysis (area %). In addition 394 g high boiling oil was recovered.

Example 6

Example 4 was repeated using 3582 g MV31, 240 g oxygen, and 14 g $BF_3$ at 85° C. Work up according to method a) without the fractionation resulted in 3131 g crude ester containing 2% MV31, 8% methanol, 22% $CF_3OCF_2CF_2COOCH_3$ and 62% $CF_3O(CF_2)_3OCF_2COOCH_3$ (GC, area %). In addition 405 g high boiling oil was recovered.

Example 7

3778 g MV31, 228 g oxygen, and 4 g $BF_3$ were reacted at 85° C. Work up according to method b) using 1558 g methanol and 642 g triethylamine, followed by a flash distillation of the lower phase resulted in 2957 g crude ester containing 5% MV31, 6% methanol, 19% $CF_3OCF_2CF_2COOCH_3$, and 50% $CF_3O(CF_2)_3OCF_2COOCH_3$ (GC, area %). The amount of high boiling oil was 433 g.

Example 8

3582 g MV31 and 216 g oxygen were reacted in the presence of 40 g $B(OCH_3)_3$ and 60 g of methanol at 85° C. Work up by method b) using 1600 g methanol and 640 g triethylamine resulted in a two phase mixture. The phases were separated and the upper phase was diluted with about 20 weight % of water. The resulting lower phase was combined with the lower phase from the reactor resulting a total amount of 3554 g. Flash distillation in the presence of water methanol and sulphuric acid gave 3502 g crude ester containing 20% MV31, 4% methanol, 21% $CF_3OCF_2CF_2COOCH_3$ and 45% $CF_3O(CF_2)_3OCF_2COOCH_3$ (GC, area %). 322 g high boiling oil were received as well.

Example 9

3581 g MV31, 248 g oxygen, 16 g $BF_3$, and 9 g water were converted at 85° C. Work up with 1600 g methanol and 641 g triethylamine resulted in 3552 g lower phase after addition of water to the upper phase. Flash distillation according to example 8 gave 3296 g crude ester containing 7% MV31, 6% methanol, 19% $CF_3OCF_2CF_2COOCH_3$, and 58% $CF_3O(CF_2)_3OCF_2COOCH_3$ (GC, area %). 403 g high boiling oil were isolated as well.

Example 10

3577 g MV31, 240 g oxygen, and 10 g $BF_3$ were converted at 85° C. The resulting acid fluoride containing mixture reacted at 20-40° C. with 3000 g of 40% aqueous KOH resulting in a three phase product mix consisting of two aqueous phases and a heavy fluoroorganic phase. The aqueous phases were separated (lower phase 3436 g, upper phase 2435 g). The lower aqueous phase was diluted with 710 g water and reacted with 700 g methanol, 1670 g $H_2SO_4$. Distillation of the reaction mixture resulted in two phase distillate. The upper phase was returned to the distillation flask and the lower phase was separated. In total, 2610 g fluoroorganic lower phase was received consisting of 2% methanol, 26% $CF_3OCF_2CF_2COOCH_3$, and 66% $CF_3O(CF_2)_3OCF_2COOCH_3$ (GC, area %).

Example 11

87.9 kg MV31 was reacted with 5.5 kg oxygen in the presence of 554 g $BF_3$ and 100 g methanol at 85° C. Work up was carried out according to b) using 39.25 kg methanol and 15.1 kg triethylamine. 12 kg of water was added to the reaction mixture while stirring. The lower phase of the resulting two phase mixture was separated (91.315 kg). An aliquot of 558 g lower phase was flash distilled after addition of methanol, water, and sulphuric acid. 479 g ester phase were received along with 79.5 g high boiling oil. The composition of the ester phase was 5% MV31, 8% methanol, 20% $CF_3OCF_2CF_2COOCH_3$, and 61% $CF_3O(CF_2)_3OCF_2COOCH_3$ (GC, area %).

Example 12

3581 g MV31, 248 g oxygen, 20 g $BF_3$, and 52 g $CH_3OCF_2CF_2H$ were reacted at 85° C. Work up according to example 7 resulted in 3297 g flash distilled ester and 403 g high boiling oil. Analysis of the ester gave 7% MV31, 6% methanol, 19% $CF_3OCF_2CF_2COOCH_3$, and 58% $CF_3O(CF_2)_3OCF_2COOCH_3$ (GC, area %).

What is claimed is:

1. A process comprising reacting, at a reaction temperature, a fluorinated ether of the formula (I)

$$R_f\text{—}O\text{—}(CF_2)_a\text{—}CF\text{=}CF_2 \qquad (I)$$

wherein $R_f$ is a fluorinated linear or branched aliphatic group and a is either 1 or 2, with an oxygen-containing gas in the presence of a catalytic amount of graphite intercalated by a Lewis acid to yield a fluorinated oxy-carboxylic acid fluoride according to formula (II):

$$R'_f\text{—}O\text{—}(CF_2)_b CF_2 COF \qquad (II)$$

wherein $R'_f$ is b fluorinated linear or branched aliphatic group and a is either 1 or 0.

2. The process of claim 1 wherein the Lewis acid is $SbF_5$.

3. The process of claim 1 wherein the reaction temperature is from about 70 to 100° C.

4. The process of claim 1 wherein $R_f$ is given by the formula (III)

$$A\text{-}(OCF(R^2_f)CF_2)_n\text{—}(O(CF_2)_m)_p\text{—} \qquad (III)$$

where each n is from 0 to 10; each m is from 1 to 10, each p is from 0 to 10; A is selected from X and $XC_aF_{2a}$, where X is selected from a halogen, hydrogen, and a functional group, the functional group selected from $SO_2Y$ with Y being F or Cl, and COOR' with R' being an alkyl group having from 1 to 6 carbon atoms and a is from 1 to 10; and $R^2_f$ is a fluorinated aliphatic group of from 1 to 10 carbon atoms.

5. The process of claim 4 wherein X is F and a is from 1 to 4.

6. The process of claim 4 wherein X is F, a is from 1 to 4, and m is from 1 to 4.

7. The process of claim 4 wherein n is 0.

8. The process of claim 4 wherein X is selected from Br and F.

9. The process of claim 1 further comprising converting the fluorinated oxy-carboxylic acid fluoride to a derivative selected from a carboxylic acid, an ester, an amide, and a carboxylate salt.

10. The process of claim 1 further comprising controlling the reaction temperature such that the reaction temperature changes by no more than 5° C. during the course of the reaction.

11. The process of claim 1 wherein the graphite intercalated by $SbF_5$ is present in an amount of from 0.01 to 20 mol % based upon the total amount of fluorinated ether used in the reaction.

* * * * *

UNITED STATES PATENT AND TRADEMARK OFFICE
CERTIFICATE OF CORRECTION

PATENT NO. : 8,394,989 B2  
APPLICATION NO. : 12/677339  
DATED : March 12, 2013  
INVENTOR(S) : Werner Schwertfeger Page 1 of 1

It is certified that error appears in the above-identified patent and that said Letters Patent is hereby corrected as shown below:

In the Specifications:

Column 1  
Line 6, Delete "APPLICATION" and insert -- APPLICATIONS --, therefor.  
Line 8, Delete "±U.S.C." and insert -- 35 U.S.C, --, therefor.

Column 2  
Line 4, Delete "CO" and insert -- Cl) --, therefor.

Column 3  
Line 16, Delete "A′O–" and insert -- A′– --, therefor.

Column 7  
Line 39, Delete "BF3" and insert -- $BF_3$ --, therefor.

Signed and Sealed this  
Fourth Day of June, 2013

Teresa Stanek Rea  
*Acting Director of the United States Patent and Trademark Office*